United States Patent
Tanimura et al.

(10) Patent No.: US 9,745,392 B2
(45) Date of Patent: Aug. 29, 2017

(54) METHOD FOR PRODUCING WATER-ABSORBENT RESIN PARTICLE

(71) Applicant: SUMITOMO SEIKA CHEMICALS CO., LTD., Kako-gun, Hyogo (JP)

(72) Inventors: Kenji Tanimura, Himeji (JP); Ryusuke Umeza, Himeji (JP); Hidenobu Kakimoto, Himeji (JP); Hideki Matsushita, Himeji (JP); Takahiro Imai, Himeji (JP)

(73) Assignee: SUMITOMO SEIKA CHEMICALS CO., LTD., Kako-gun, Hyogo (JP)

( * ) Notice: Subject to any disclaimer, the term of this patent is extended or adjusted under 35 U.S.C. 154(b) by 0 days.

(21) Appl. No.: 15/126,327

(22) PCT Filed: Mar. 12, 2015

(86) PCT No.: PCT/JP2015/057264
§ 371 (c)(1),
(2) Date: Sep. 15, 2016

(87) PCT Pub. No.: WO2015/146603
PCT Pub. Date: Oct. 1, 2015

(65) Prior Publication Data
US 2017/0081443 A1 Mar. 23, 2017

(30) Foreign Application Priority Data
Mar. 26, 2014 (JP) .................................. 2014-064381

(51) Int. Cl.
| | | |
|---|---|---|
| C08F 2/44 | (2006.01) | |
| C08F 20/00 | (2006.01) | |
| C08F 20/06 | (2006.01) | |
| C08F 118/02 | (2006.01) | |
| C08F 120/06 | (2006.01) | |
| C08F 2/32 | (2006.01) | |
| A61L 15/24 | (2006.01) | |
| C08J 3/24 | (2006.01) | |

(52) U.S. Cl.
CPC ............ *C08F 120/06* (2013.01); *A61L 15/24* (2013.01); *C08F 2/32* (2013.01); *C08J 3/24* (2013.01); *C08J 3/245* (2013.01); *C08J 2333/02* (2013.01)

(58) Field of Classification Search
CPC .......... C08F 2/32; C08F 20/06; C08F 120/06; C08L 33/08; B01J 20/262; B01J 20/3085; A61L 15/60; A61L 15/48

USPC .................... 524/773; 526/303.1, 317.1, 319
See application file for complete search history.

(56) References Cited

U.S. PATENT DOCUMENTS

| | | | |
|---|---|---|---|
| 4,340,706 A | | 7/1982 | Obayashi et al. |
| 9,138,722 B2 * | | 9/2015 | Tanimura .................. C08F 2/32 |
| 2009/0281247 A1 * | | 11/2009 | Handa ....................... C08F 2/32 525/243 |
| 2014/0243478 A1 | | 8/2014 | Heguri et al. |

FOREIGN PATENT DOCUMENTS

| | | | |
|---|---|---|---|
| EP | 0 234 202 A1 | 9/1987 | |
| JP | S 56-026909 A | 3/1981 | |
| JP | S 56-131608 A | 10/1981 | |
| JP | S 57-128709 A | 8/1982 | |
| JP | S 57-192416 A | 11/1982 | |
| JP | S 58-179201 A | 10/1983 | |
| JP | S 62-172006 A | 7/1987 | |
| JP | H 01-294703 A | 11/1989 | |
| JP | H 08-120014 A | 5/1996 | |
| JP | 2007-049948 A | 3/2007 | |
| JP | 2012-007062 A | 1/2012 | |
| WO | 2013/051417 A1 | 3/2015 | |

OTHER PUBLICATIONS

International Search Report for PCT/JP2015/057264 dated Jun. 9, 2015 [PCT/ISA/210].
Written Opinion for PCT/JP2015/057264 dated Jun. 9, 2015 [PCT/ISA/237].
Third Party Observation for PCT/JP2015/057264 dated Jul. 1, 2016 [PCT/ISA/345].
Communication dated May 24, 2017 issued by the State Intellectual Property Office of the People's Republic of China in counterpart application No. 201580016277.6.
Zhong et al., "Synthesis of AA-AM Absorbent Resin by Inverse Suspension Polymerization", Journal of Maoming University, vol. 17, No. 3, pp. 7-10, Jun. 30, 2007 (11 pages total).

\* cited by examiner

*Primary Examiner* — William Cheung
(74) *Attorney, Agent, or Firm* — Sughrue Mion, PLLC

(57) ABSTRACT

Provided is a method for producing water-absorbent resin particles suitable for use in absorbent article and the like, the water-absorbent resin particles having better water-absorbent performance, a suitable particle size, and a narrow particle-size distribution. A method for producing water-absorbent resin particles by reversed-phase suspension polymerization of a water-soluble ethylenic unsaturated monomer in a carrier fluid, wherein the method for producing water-absorbent resin particles comprises conducting the reversed-phase suspension polymerization reaction in the presence of an organic acid monoglyceride.

18 Claims, No Drawings

METHOD FOR PRODUCING WATER-ABSORBENT RESIN PARTICLE

CROSS REFERENCE TO RELATED APPLICATIONS

This application is a National Stage of International Application No. PCT/JP2015/057264 filed Mar. 12, 2015, claiming priority based on Japanese Patent Application No. 2014-064381 filed Mar. 26, 2014, the contents of all of which are incorporated herein by reference in their entirety.

TECHNICAL FIELD

The present invention relates to a method for producing water-absorbent resin particles.

BACKGROUND ART

Water-absorbent resin particles are mainly used for disposable diapers, sanitary napkins, incontinence pads, pet sheets, water-retaining materials for soil, water-blocking materials for power cable, dew condensation prevention agents, and the like. Absorbent articles, for example, disposable diapers, are typically formed such that an absorbent material composed of water-absorbent resin particles and hydrophilic fibers is sandwiched between a liquid-permeable sheet to be in contact with the body and a liquid-impermeable sheet provided on the opposite side. The absorbent material is produced, for example, by allowing a mixture including water-absorbent resin particles and crushed hydrophilic fiber to be layered on a metal mesh by means of an air flow, and then, allowing the layered product to be compressed by pressing.

Examples of known water-absorbent resin particles include hydrolysates of starch-acrylonitrile graft copolymers, neutralized products of starch-acrylic acid graft copolymers, saponified products of vinyl acetate-acrylic acid ester copolymers, crosslinked products of partially neutralized polymers of acrylic acid, and partially neutralized polyacrylic acids.

The water-absorbent resin particles used in absorbent materials are required to exhibit not only an excellent water-absorption capacity and water-retention capacity, but also suitable particle size and narrow particle size distribution. When particles with a large particle size are dominantly present, the absorbent material, when compressed, is likely to become hard. When particles with a small particle size are dominantly present, the particles pass through the metallic mesh in the process of producing the absorbent material; thus, such particles are not preferable. Specifically, the water-absorbent resin particles used in absorbent materials are desired to have a median particle size suitable for the design of the intended absorbent materials or absorbent articles, and narrow particle size distribution.

From the standpoint of high performance of the resulting water-absorbent resin particles and the simplicity of the production method, polymerization of a water-soluble ethylenically unsaturated monomer is the mainstream method for producing water-absorbent resin particles. Examples of the polymerization method include an aqueous solution polymerization method comprising polymerizing an aqueous solution of a water-soluble ethylenically unsaturated monomer to obtain a water-containing gel, milling the gel, and drying the gel; and a reversed-phase suspension polymerization method comprising dispersing a water-soluble ethylenically unsaturated monomer in the presence of a dispersion stabilizer in an organic dispersion medium, such as a hydrocarbon dispersion medium, for suspension polymerization to thereby obtain a water containing-gel, dehydrating the gel, and drying the gel.

In the aqueous solution polymerization method, the water-containing gel obtained after polymerization is in the form of viscous block-shaped material, which therefore make the milling step and drying step complicated, increasing the likelihood of the generation of fine particles in the milling step; this lowers the possibility of obtaining water-absorbent resin particles with a suitable particle size and narrow particle size distribution. In the reversed-phase suspension polymerization method, however, it is possible to control the size of the particles by adjusting the size of the droplets of the water-soluble ethylenically unsaturated monomer dispersed in a dispersion medium. Thus, there has been proposed a variety of techniques for controlling the particle size based on the reversed-phase suspension polymerization method.

Examples of proposed techniques for achieving narrow particle size distribution include a polymerization method performed under reduced pressured using a sorbitol fatty acid ester as a dispersion stabilizer (Patent Literature 1), a method using a sorbitan fatty acid ester with an HLB of 8 to 12 as a dispersion stabilizer (Patent Literature 2), and a method using a polyglycerol fatty acid ester as a dispersion stabilizer (Patent Literature 3). However, even these techniques have not been capable to provide water-absorbent resin particles that exhibit satisfactory performance from the standpoint of excellent water-absorption ability, suitable particle size, and narrow particle size distribution.

PRIOR ART LITERATURE

Patent Literature

Patent Literature 1: JPS56-26909A
Patent Literature 2: JPS56-131608A
Patent Literature 3: JPS62-172006A

SUMMARY OF INVENTION

Technical Problem

An object of the present invention is to provide a method for producing water-absorbent resin particles that exhibit a suitable particle size and narrow particle size distribution as well as an excellent water-absorption ability, and that can suitably be used in absorbent articles and the like.

Solution to Problem

The present inventors found that in producing water-absorbent resin particles through reversed-phase suspension polymerization, the use of an organic acid monoglyceride as a dispersion stabilizer can provide water-absorbent resin particles that exhibit a suitable particle size and narrow particle size distribution as well as an excellent water-absorption ability, and that can suitably be used in absorbent articles and the like. The inventors then completed the invention.

Specifically, the present invention relates to a method for producing water-absorbent resin particles by subjecting a water-soluble ethylenically unsaturated monomer to reversed-phase suspension polymerization in a dispersion medium, the method comprising performing the reversed-phase suspension polymerization in the presence of an organic acid monoglyceride.

Specifically, the present invention includes, for example, the subject matter described in the following items.

Item 1. A method for producing water-absorbent resin particles by subjecting a water-soluble ethylenically unsaturated monomer to reversed-phase suspension polymerization in a dispersion medium, the method comprising performing the reversed-phase suspension polymerization in the presence of an organic acid monoglyceride.

Item 2. The method for producing water-absorbent resin particles according to Item 1, wherein the reversed-phase suspension polymerization is performed in the presence of an organic acid monoglyceride having one ester group in which a fatty acid having 10 to 18 carbon atoms is ester-bonded with one hydroxyl group of the glycerol, and one or two ester groups in which an organic acid having 2 to 8 carbon atoms is ester-bonded with one or two hydroxyl groups of the glycerol.

Item 3. The method for producing water-absorbent resin particles according to Item 2, wherein the fatty acid having 10 to 18 carbon atoms is at least one member selected from the group consisting of capric acid, lauric acid, myristic acid, palmitic acid, stearic acid, and oleic acid.

Item 4. The method for producing water-absorbent resin particles according to Item 2 or 3, wherein the organic acid having 2 to 8 carbon atoms is at least one member selected from the group consisting of acetic acid, lactic acid, citric acid, succinic acid, and diacetyl tartaric acid.

Item 5. The method for producing water-absorbent resin particles according to any one of Items 1 to 4, wherein the organic acid monoglyceride is at least one member selected from the group consisting of glyceryl monolaurate acetate, glyceryl monostearate acetate, glyceryl monostearate lactate, glyceryl monostearate citrate, and glyceryl monooleate citrate.

Item 6. The method for producing water-absorbent resin particles according to any one of Items 1 to 5, wherein the amount of the organic acid monoglyceride is 0.1 to 30 parts by mass per 100 parts by mass of the water-soluble ethylenically unsaturated monomer.

Item 7. The method for producing water-absorbent resin particles according to any one of Items 1 to 6, wherein the reversed-phase suspension polymerization is performed in the presence of a radical polymerization initiator.

Item 8. The method for producing water-absorbent resin particles according to any one of Items 1 to 7, wherein the dispersion medium is a hydrocarbon dispersion medium (preferably, a hydrocarbon containing at least one member selected from the group consisting of n-hexane, n-heptane, cyclohexane, and isomers thereof).

Item 9. The method for producing water-absorbent resin particles according to any one of Items 1 to 8, the method comprising, after the reversed-phase suspension polymerization, adding a crosslinking agent to perform post-crosslinking.

Item 10. The method for producing water-absorbent resin particles according to any one of Items 1 to 9, wherein the water-soluble ethylenically unsaturated monomer is at least one member selected from the group consisting of (meth)acrylic acid, salts thereof, (meth)acrylamide, and N,N-dimethyl(meth)acrylamide (preferably (meth)acrylic acid and salts thereof).

Advantageous Effects of Invention

The present invention can produce, by using an organic acid monoglyceride as a dispersion stabilizer, water-absorbent resin particles that exhibit a suitable particle size and narrow particle size distribution as well as an excellent water-absorption ability, and that can suitably be used in absorbent articles and the like.

DESCRIPTION OF EMBODIMENTS

A feature of the method for producing water-absorbent resin particles of the present invention is that in the method for producing water-absorbent resin particles by subjecting a water-soluble ethylenically unsaturated monomer to reversed-phase suspension polymerization in a dispersion medium, the reversed-phase suspension polymerization is performed in the presence of an organic acid monoglyceride.

In the reversed-phase suspension polymerization, a multistep polymerization including two or more steps can be performed by further adding a water-soluble ethylenically unsaturated monomer to the water-absorbent resin particles obtained by reversed-phase suspension polymerization. In the multistep polymerization including two or more steps, the particle size of the resulting water-absorbent resin particles can be increased by allowing the particles obtained in the reversed-phase suspension polymerization of the first step to agglomerate. This makes it easier to achieve a particle size suitable for absorbent articles, such as disposable diapers.

Examples of water-soluble ethylenically unsaturated monomers for use in the present invention include (meth)acrylic acid (in this specification, "acrylic" and "methacrylic" are collectively referred to as "(meth)acrylic"; the same applies hereinafter) and salts thereof; 2-(meth)acrylamide-2-methylpropane sulfonic acid and salts thereof; nonionic monomers, such as (meth)acrylamide, N,N-dimethyl(meth)acrylamide, 2-hydroxyethyl(meth)acrylate, N,N-methylol(meth)acrylamide, and polyethylene glycol mono(meth)acrylate; and amino group-containing unsaturated monomers, such as N,N-diethylaminoethyl(meth)acrylate, N,N-diethylaminopropyl(meth)acrylate, and diethylaminopropyl(meth)acrylamide, and quaternary compounds thereof. These water-soluble ethylenically unsaturated monomers may be used alone, or in a combination of two or more.

Of the water-soluble ethylenically unsaturated monomers, (meth)acrylic acid and salts thereof, (meth)acrylamide, and N,N-dimethyl(meth)acrylamide are preferably used from the standpoint of industrial availability. Moreover, from the standpoint of high water-absorption ability of the resulting water-absorbent resin particles, (meth)acrylic acid and salts thereof are more preferably used.

In performing a multistep polymerization including two or more steps, the water-soluble ethylenically unsaturated monomer used in the second and subsequent steps may be the same as or different from the water-soluble ethylenically unsaturated monomer used in the first step.

When the water-soluble ethylenically unsaturated monomer is subjected to reversed-phase suspension polymerization, the water-soluble ethylenically unsaturated monomer may be used as an aqueous solution to enhance the efficiency of the dispersion of the monomer in the dispersion medium. The concentration of the water-soluble ethylenically unsaturated monomer in the aqueous solution is not particularly limited, but typically 20% by mass or more to the saturation concentration or less, preferably 25 to 70% by mass, and more preferably 30 to 55% by mass.

When the water-soluble ethylenically unsaturated monomer contains acid groups, like (meth)acrylic acid or 2-(meth)acrylamide-2-methylpropane sulfonic acid, the acid groups of the water-soluble ethylenically unsaturated monomer for use may optionally be neutralized with an alkaline neutralizer beforehand. The alkaline neutralizer is not particularly limited, but examples of the neutralizer include alkali metal salts, such as sodium hydroxide, sodium carbonate, sodium hydrogen carbonate, potassium hydroxide, and potassium carbonate; and ammonia. The alkaline neutralizer for use may be in the form of an aqueous solution to simplify the neutralizing operation. These alkaline neutralizers may be used alone, or in a combination of two or more.

The degree of neutralization of the water-soluble ethylenically unsaturated monomer with the alkaline neutralizer is not particularly limited. However, to increase the osmotic pressure of the obtained water-absorbent resin particles and thereby increase the water-absorption ability, while avoiding safety concerns attributed to an excess amount of the alkaline neutralizer, the degree of neutralization relative to all acid groups contained in the water-soluble ethylenically unsaturated monomer is preferably 10 to 100 mol %, and more preferably 30 to 80 mol %.

The reversed-phase suspension polymerization of the present invention is preferably performed in the presence of a radical polymerization initiator to suitably shorten the time period required for the polymerization reaction. Examples of radical polymerization initiators for use in the present invention include persulfates, such as potassium persulfate, ammonium persulfate, and sodium persulfate; peroxides, such as methyl ethyl ketone peroxide, methyl isobutyl ketone peroxide, di-t-butyl peroxide, t-butyl cumyl peroxide, t-butyl peroxyacetate, t-butylperoxy isobutyrate, t-butylperoxy pivalate, and hydrogen peroxide; and azo compounds, such as 2,2'-azobis(2-amidinopropane) dihydrochloride, 2,2'-azobis[2-(N-phenyl amidino)propane] dihydrochloride, 2,2'-azobis[2-(N-allyl amidino)propane] dihydrochloride, 2,2'-azobis{2-[1-(2-hydroxyethyl)-2-imidazoline-2-yl]propane}dihydrochloride, 2,2'-azobis{2-methyl-N-[1,1-bis(hydroxymethyl)-2-hydroxyethyl] propionamide}, 2,2'-azobis[2-methyl-N-(2-hydroxyethyl)-propionamide], and 4,4'-azobis(4-cyanovaleric acid).

Of these radical polymerization initiators, potassium persulfate, ammonium persulfate, sodium persulfate, and 2,2'-azobis(2-amidinopropane)dihydrochloride are preferably used from the standpoint of availability and easy handling. These radical polymerization initiators may used alone, or in a combination of two or more.

In the use of the radical polymerization initiator, the amount of the initiator is preferably 1 mole or less per 100 moles of the water-soluble ethylenically unsaturated monomer in each polymerization step to prevent rapid polymerization reaction. The lower limit of the amount of the radical polymerization initiator is not particularly limited. For example, the use of 0.005 moles or more of the radical polymerization initiator per 100 moles of the water-soluble ethylenically unsaturated monomer in each polymerization step can suitably shorten the period required for the polymerization reaction.

The radical polymerization initiator may be combined with a reducing agent, such as sodium sulfite, sodium hydrogen sulfite, ferrous sulfate, and L-ascorbic acid, to use the initiator as a redox polymerization initiator.

To control the water-absorption ability of the water-absorbent resin particles, a chain transfer agent may be added. Examples of chain transfer agents include hypophosphites, thiols, thiol acids, secondary alcohols, and amines.

A crosslinking agent may optionally be added to the water-soluble ethylenically unsaturated monomer to perform polymerization. Examples of crosslinking agents to be added to the water-soluble ethylenically unsaturated monomer before a polymerization reaction (internal crosslinking agent) include compounds having two or more polymerizable unsaturated groups, such as unsaturated polyesters obtained by reacting polyols, such as diols and triols including (poly)ethylene glycol (in this specification, "polyethylene glycol" and "ethylene glycol" are collectively referred to as "(poly)ethylene glycol." The same applies to "(poly)" hereinafter), (poly)propylene glycol, 1,4-butanediol, trimethylolpropane, and (poly)glycerol, with unsaturated acids, such as (meth)acrylic acid, maleic acid, and fumaric acid; bisacrylamides, such as N,N'-methylenebisacrylamide; di- or tri(meth)acrylic acid esters obtained by reacting polyepoxide with (meth)acrylic acid; di(meth)acrylic acid carbamyl esters obtained by reacting polyisocyanates, such as tolylene diisocyanate and hexamethylene diisocyanate, with (meth)acrylic acid hydroxyethyl; allylated starch, allylated cellulose, diallyl phthalate, N,N',N"-triallyl isocyanurate, and divinylbenzene; and compounds having two or more reactive functional groups, such as polyglycidyl compounds, such as diglycidyl compounds including (poly)ethylene glycol diglycidyl ether, (poly)propylene glycol diglycidyl ether, and (poly)glycerol diglycidyl ether, and triglycidyl compounds; epihalohydrin compounds, such as epichlorohydrin, epibromohydrin, and α-methyl epichlorohydrin; isocyanate compounds, such as 2,4-tolylene diisocyanate and hexamethylene diisocyanate; and oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol. These internal crosslinking agents may be used alone, or in a combination of two or more.

When the internal crosslinking agent is used, the amount of the agent is preferably 0.00001 to 1 mole, and more preferably 0.0001 to 0.5 moles, per 100 moles of the water-soluble ethylenically unsaturated monomer in each polymerization step, in order to sufficiently enhance the water-absorption ability of the resulting water-absorbent resin particles.

To adjust the particle size of the resulting water-absorbent resin particles, a thickener may optionally be added to an aqueous solution of the water-soluble ethylenically unsaturated monomer. Examples of thickeners include hydroxyethyl cellulose, hydroxypropyl cellulose, methyl cellulose, carboxymethyl cellulose, polyacrylic acid, (partly) neutralized polyacrylic acid, polyethylene glycol, polyacrylamide, polyethyleneimine, dextrin, sodium alginate, polyvinyl alcohol, polyvinyl pyrrolidone, and polyethylene oxide. Typically in reversed-phase suspension polymerization, at the same stirring rotation speed for polymerization, the higher the viscosity of the water-soluble ethylenically unsaturated monomer aqueous solution, the more likely the particle size of the resulting water-absorbent resin particles becomes larger.

When the thickener is used, the amount of the agent cannot be uniformly determined because of the variation of the obtained viscosity of the monomer aqueous solution, depending on the type of thickener; however, the amount of the agent is preferably 0.005 to 10 parts by mass, and more preferably 0.01 to 5 parts by mass, per 100 parts by mass of the water-soluble ethylenically unsaturated monomer used in the first-step polymerization, from the standpoint of the particle size adjustment of the resulting water-absorbent resin particles.

In the present invention, a hydrocarbon dispersion medium is preferable as a dispersion medium. Examples of hydrocarbon dispersion media include aliphatic hydrocarbons having 6 to 8 carbon atoms, such as n-hexane, n-heptane, 2-methylhexane, 3-methylhexane, 2,3-dimethylpentane, 3-ethylpentane, and n-octane; alicyclic hydrocarbons, such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons, such as benzene, toluene, and xylene. These dispersion media may be used alone, or in a combination of two or more. Of these dispersion media, n-hexane, n-heptane, and cyclohexane are preferably used from the standpoint of industrial availability, stable quality, and inexpensive prices. Hydrocarbon dispersion media, such as n-hexane, n-heptane, cyclohexane, and isomers thereof, and mixed hydrocarbons containing at least two members selected from the group consisting of n-hexane, n-heptane, cyclohexane, and isomers thereof are also preferably used. As an example of the mixed dispersion media described above, commercially available Exxsol Heptane (Exxon Mobil Corporation: containing 75 to 85% by mass of hydrocarbons, i.e., heptane and its isomer) may be used, and it will also give preferable results.

The amount of the dispersion medium is preferably 100 to 1,500 parts by mass, and more preferably 200 to 1,400 parts by mass, per 100 parts by mass of the water-soluble ethylenically unsaturated monomer used in the first-step polymerization, from the standpoint of easy removal of the polymerization heat and easy control of the polymerization temperature. The phrase "the first-step polymerization" refers to the step in single-step polymerization and the first-step polymerization in multistep polymerization containing two or more steps.

The most notable feature of the present invention is that in a method for producing water-absorbent resin particles by subjecting a water-soluble ethylenically unsaturated monomer to reversed-phase suspension polymerization in a dispersion medium (preferably in a hydrocarbon dispersion medium), the reversed-phase suspension polymerization is performed in the presence of an organic acid monoglyceride. The organic acid monoglyceride suitably enhances the dispersion stability of the water-soluble ethylenically unsaturated monomer in the dispersion medium.

In the present invention, the organic acid monoglyceride refers to an organic acid ester of monoglyceride (a glycerol fatty acid ester). In other words, the organic acid monoglyceride refers to a compound in which fatty acid (A) is ester-bonded with one of three hydroxyl groups of glycerol, and organic acid (B) is ester-bonded with the remaining hydroxyl groups. The number of organic acid (B) bonded with the remaining hydroxyl groups may be one or two per molecule of glycerol. The organic acid monoglyceride for use may also be a mixture of a compound in which one molecule of organic acid (B) is ester-bonded with one molecule of glycerol, and a compound in which two molecules of organic acid (B) are ester-bonded with one molecule of glycerol.

As fatty acid (A), fatty acids having 10 to 18 carbon atoms are preferable. Specific examples include capric acid, lauric acid, myristic acid, palmitic acid, stearic acid, and oleic acid.

Examples of organic acid (B) include monocarboxylic acids, dicarboxylic acids, and tricarboxylic acids. As long as the group "—COOH" is contained, substituents other than the carboxyl group may also be contained. Examples of containable substituents other than the carboxyl group include hydroxyl group and acetyloxy group. As organic acid (B), carboxylic acid compounds listed above as fatty acid (A) may also be used. As organic acid (B), organic acids having 2 to 8 carbon atoms are preferable. Specific examples include acetic acid, lactic acid, citric acid, succinic acid, and diacetyl tartaric acid.

The hydrophilic-lipophilic balance (HLB) of the organic acid monoglyceride is preferably 2 to 17, and more preferably 2 to 10, to allow the organic acid monoglyceride to dissolve in a dispersion medium (preferably a hydrocarbon dispersion medium) and to enhance the dispersion stability of the water-soluble ethylenically unsaturated monomer.

The organic acid monoglyceride is not particularly limited as long as it falls within the scope described above. Examples include glyceryl monolaurate acetate, glyceryl monostearate acetate, glyceryl monostearate lactate, glyceryl monostearate succinate, glyceryl monostearate diacetyl tartaric acid ester, glyceryl monostearate citrate, and glyceryl monooleate citrate. Of these, glyceryl monolaurate acetate, glyceryl monostearate acetate, glyceryl monostearate lactate, glyceryl monostearate citrate, and glyceryl monooleate citrate are preferably used from the standpoint of the dispersion stability of the water-soluble ethylenically unsaturated monomer in a dispersion medium. These organic acid monoglycerides may be used alone, or in a combination of two or more. These organic acid monoglycerides can be produced, for example, by esterifying a monoglyceride (a glycerol fatty acid ester) with an organic acid. Commercially available organic acid monoglycerides may also be used unmodified. Examples of commercially available products include Poem G-002 (Riken Vitamin Co., Ltd.); and Sunsoft No. 621B and Sunsoft No. 661AS (Taiyo Kagaku Co., Ltd.).

As long as the dispersion stability achieved by the organic acid monoglyceride is not impaired, other dispersion stabilizer(s) may also be used in combination. Examples of dispersion stabilizers for combination use include sucrose fatty acid esters, polyglycerol fatty acid esters, and sorbitan fatty acid esters.

In addition, as a dispersion stabilizer, a polymeric dispersion stabilizer may be used in combination with the organic acid monoglyceride. Examples of polymeric dispersion stabilizers for use include maleic anhydride modified polyethylene, maleic anhydride modified polypropylene, and maleic anhydride modified ethylene-propylene copolymers. These polymeric dispersion stabilizers may be used alone, or in a combination of two or more.

The amount of the organic acid monoglyceride is preferably 0.1 parts by mass or more, more preferably 0.3 parts by mass or more, and particularly more preferably 0.5 parts by mass or more, per 100 parts by mass of the water-soluble ethylenically unsaturated monomer in the first-step polymerization from the standpoint of maintaining an excellent dispersion state of the water-soluble ethylenically unsaturated monomer in a dispersion medium. To obtain a dispersion effect that meets the amount of the organic acid monoglyceride used, the amount is preferably 30 parts by mass or less, more preferably 20 parts by mass or less, and particularly more preferably 5 parts by mass or less, per 100 parts by mass of the water-soluble ethylenically unsaturated monomer used in the first-step polymerization. For example, about 1.2 parts by mass of the organic acid monoglyceride per 100 parts by mass of the water-soluble ethylenically unsaturated monomer can be used.

When the polymeric dispersion stabilizer is used, the amount of the stabilizer is preferably 0.1 to 30 parts by mass, and more preferably 0.3 to 20 parts by mass, per 100 parts by mass of the water-soluble ethylenically unsaturated monomer in the first-step polymerization.

The reaction temperature for the polymerization reaction cannot be uniformly determined because of its variation depending on the presence or absence of a radical polymerization initiator and the type of the initiator; however, the reaction temperature is preferably 20 to 110° C., and more preferably 40 to 90° C. from the standpoint that profitability may be improved by allowing prompt progress of a polymerization to reduce a polymerization time, and polymerization heat may be easily removed to perform a smooth reaction. The reaction time is preferably 0.1 hours to 4 hours. The polymerization reaction is preferably performed in an inert gas atmosphere, such as nitrogen or argon, as necessary.

In the present invention, when a multistep polymerization including two or more steps is performed, the polymerization reaction in the second and subsequent steps may be performed by further adding the water-soluble ethylenically unsaturated monomer to the water-absorbent resin particles obtained by reversed-phase suspension polymerization. When the water-soluble ethylenically unsaturated monomer is further added, the radical polymerization initiator and/or the internal crosslinking agent described above may also be further added. The amounts of the radical polymerization initiator and the internal crosslinking agent added in the second and subsequent steps are as described above.

In the present invention, it is preferable to incorporate a post-crosslinking step of adding a crosslinking agent anytime after polymerization of the water-soluble ethylenically unsaturated monomer to allow for a reaction. Performing a post-crosslinking step after polymerization enhances the water-absorption ability, such as water-retention capacity, thus providing water-absorbent resin particles suitable for absorbent articles, such as disposable diapers.

Examples of crosslinking agents for use in a post-crosslinking step (post-crosslinking agents) include compounds having at least two reactive functional groups. Examples of the compound include polyols, such as ethylene glycol, propylene glycol, 1,4-butanediol, trimethylolpropane, glycerol, polyoxyethylene glycol, polyoxy propylene glycol, and polyglycerol; polyglycidyl compounds, such as (poly)ethylene glycol diglycidyl ether, (poly)glycerol diglycidyl ether, (poly)glycerol triglycidyl ether, (poly)propylene glycol polyglycidyl ether, and (poly)glycerol polyglycidyl ether; halo-epoxy compounds, such as epichlorohydrin, epibromohydrin, and α-methyl epichlorohydrin; isocyanate compounds, such as 2,4-tolylene diisocyanate, and hexamethylene diisocyanate; oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds, such as 1,2-ethylene bisoxazoline; carbonate compounds, such as ethylene carbonate; and hydroxy alkylamide compounds, such as bis[N,N-di(β-hydroxyethyl)] adipamide. Of these post-crosslinking agents, polyglycidyl compounds, such as (poly)ethylene glycol diglycidyl ether, (poly)glycerol diglycidyl ether, (poly)glycerol triglycidyl ether, (poly)propylene glycol polyglycidyl ether, and (poly)glycerol polyglycidyl ether are preferably used. These post-crosslinking agents may be used alone, or in a combination of two or more.

When the post-crosslinking agent is used, the amount of the agent is preferably 0.001 to 1 mole, and more preferably 0.005 to 0.5 moles, based on the total amount of the water-soluble ethylenically unsaturated monomer used for polymerization, which is taken as 100 moles, from the standpoint of the enhancement of the water-absorption ability, such as water-retention capacity, of the resulting water-absorbent resin particles.

The timing for adding the post-crosslinking agent is not particularly limited, as long as the agent is added anytime after polymerization.

Examples of methods for adding the post-crosslinking agent include a method comprising adding a post-crosslinking agent as it is, a method comprising adding an aqueous solution of the agent, and a method comprising adding a solution of the agent in a hydrophilic organic solvent. Examples of the hydrophilic organic solvent include lower alcohols, such as methyl alcohol, ethyl alcohol, n-propyl alcohol, isopropyl alcohol, and propylene glycol; ketones, such as acetone, and methyl ethyl ketone; ethers, such as diethyl ether, dioxane, and tetrahydrofuran; amides, such as N,N-dimethyl formamide; and sulfoxides, such as dimethyl sulfoxide. These hydrophilic organic solvents may be used alone or in a combination of two or more, and may also be used as a mixture solvent with water.

The method for adding the post-crosslinking agent is not particularly limited. Examples of the addition method include a method comprising adding a post-crosslinking agent (post-crosslinking agent solution) to a water-containing gel obtained by dispersing the water-absorbent resin particles in a dispersion medium; and a method comprising evaporating the dispersion medium and then spraying the post-crosslinking agent (post-crosslinking agent solution) using a spray while stirring powdery water-absorbent resin particles.

The post-crosslinking agent may be added, for example, in the presence of preferably 1 to 400 parts by mass of water, more preferably 5 to 200 parts by mass of water, and still more preferably 10 to 100 parts by mass of water, per 100 parts by mass of the water-soluble ethylenically unsaturated monomer.

The temperature for the post-crosslinking step is preferably 50 to 250° C., more preferably 60 to 180° C., and still more preferably 70 to 150° C. The time period for the post-crosslinking step cannot be uniformly determined because of the variation depending on the reaction temperature, the type and the amount of the post-crosslinking agent, and the like; however, the time period is typically 1 to 300 minutes, and preferably 5 to 200 minutes.

The present invention may optionally comprise, after polymerization, a drying step of externally adding energy such as heat to remove water, the dispersion medium, and the like, by distillation. The drying step may be performed under ordinary pressure, or under reduced pressure, and also under air stream, such as nitrogen, to increase the drying efficiency; these methods may also be combined. When the drying step is performed under ordinary pressure, the drying temperature is preferably 70 to 250° C., more preferably 80 to 180° C., and still more preferably 80 to 140° C. When the drying step is performed under reduced pressure, the drying temperature is preferably 60 to 100° C., and more preferably 70 to 90° C.

Additives, such as a lubricant, a deodorizer, and an anti-bacterial agent, may be further added to the water-absorbent resin particles of the present invention, depending on the intended use. The thus-obtained water-absorbent resin particles can be suitably used in absorbent materials and water-absorbent articles using the absorbent materials, because of the excellent water-absorption ability, suitable particle size, and narrow particle size distribution.

The water-retention capacity of physiological saline, median particle size, and uniformity degree of particle size distribution of water-absorbent resin particles are measured by the methods described below.

The water-retention capacity of physiological saline of the water-absorbent resin particles obtained by the production method of the present invention is preferably 20 g/g or more, more preferably 25 g/g or more, and still more preferably 30 g/g or more from the standpoint of increasing the absorption capacity of the absorbent material used in absorbent articles.

The median particle size of the water-absorbent resin particles obtained by the production method of the present invention cannot be uniformly limited because of the variation depending on the intended use; however, the median particle size is, for example, about 10 to 800 μm. When the particles are used, for example, in shin sheet products, such as water-blocking materials for power cable, particles having a small median particle size of about 20 to 200 μm are selected. When the water-absorbent resin particles and hydrophilic fibers are mixed to prepare an absorbent material for use in absorbent articles, such as disposable diapers, particles having a relatively large median particle size of about 200 to 600 μm are selected.

The particle size distribution of the water-absorbent resin particles is preferably narrow. Small particles are unsatisfactory in powder flowability and generate dust, whereas particles with an unnecessarily large size may degrade the quality of applied products of the water-absorbent resin particles. For example, in the case of disposable diapers, water-absorbent resin particles with a small particle size are difficult to transfer in the production of absorbent materials, and may pass through a metallic mesh. With particles with a large particle size, on the other hand, the absorbent material may become hard, or give a grainy, unpleasant texture when being compressed. Thus, the uniformity degree of particle size distribution of water-absorbent resin particles, which serves as an index for indicating the narrowness of particle size distribution, is preferably 3.0 or less, more preferably 2.6 or less, and still more preferably 2.4 or less.

The water-retention capacity of physiological saline indicates the mass of physiological saline that can be absorbed by water-absorbent resin particles per unit mass (i.e., the index of water absorption capacity of water-absorbent resin particles). Specifically, the water-retention capacity of physiological saline is determined by dispersing water-absorbent resin particles in physiological saline (0.9% by mass sodium chloride aqueous solution), allowing the particles to swell, removing the water that was not absorbed by the water-absorbent resin particles by centrifugation and the like, measuring the mass of the swollen water-absorbent resin particles, and dividing the measured mass by the mass of the water-absorbent resin particles before being swollen. Specifically, the water-retention capacity of physiological saline (g/g) is a value determined by the equation:

mass (g) of water-absorbent resin particles after swelling/mass (g) of water-absorbent resin particles before swelling The median particle size indicates the particle size at 50% point of cumulative distribution obtained by integrating, in order from the larger particle size, the frequency distribution showing what percent of the total particles is present in a predetermined particle size range. Specifically, particles are sorted out using several different JIS standard sieves. Then, the proportion of particles having a particle size larger than the sieve opening is calculated as a percentage of the total mass, and a cumulative mass percentage is determined. The obtained cumulative mass percentages are then plotted on logarithmic probability paper such that each particle size corresponds to the opening size of each sieve to draw an approximate straight line, and the 50% by mass point of cumulative mass percentage on the line is determined as the median particle size. More specifically, the median particle size is calculated, for example, in accordance with the procedure in the Examples described below.

The uniformity degree of particle size distribution is calculated by determining the particle size (X1) corresponding to 15.9% by mass (cumulative mass percentage) and the particle size (X2) corresponding to 84.1% by mass (cumulative mass percentage) on the basis of the approximate straight line showing a correlation between the cumulative mass percentage and the particle size obtained in median particle size measurement, and applying the obtained values to the following equation:

uniformity degree=$X1/X2$

The uniformity degree closer to the lower limit 1.0 indicates a narrower particle size distribution.

EXAMPLES

The following Examples and Comparative Examples describe the present invention in more detail. However, the present invention is not limited to the Examples.
Evaluation Method The properties of the water-absorbent resin particles obtained in the Examples and Comparative Examples were measured and evaluated in accordance with the procedures described below.
(1) Water-Retention Capacity of Physiological Saline 500 g of a 0.9% by mass sodium chloride aqueous solution (physiological saline) was weighed and placed in a 500-mL beaker, and 2.0 g of water-absorbent resin particles was dispersed in the solution with stirring at 600 r/min so as not to form lumps. The dispersion was allowed to stand for 30 minutes while being stirred so that the water-absorbent resin particles were allowed to sufficiently swell. Thereafter, the swollen dispersion was poured into a cotton bag (cotton broadcloth No. 60, 100 mm in length×200 mm in width), and the top of the cotton bag was tied with a rubber band, followed by dehydration for 1 minute with a dehydrator (Kokusan Co., Ltd., Model No: H-122) with the centrifugal force set at 167G, thereby measuring the mass Wa (g) of the cotton bag containing the dehydrated swollen gel. The same procedure was repeated without using water-absorbent resin particles, and the empty mass Wb (g) of the cotton bag upon swelling was measured. The water-retention capacity of physiological saline of the water-absorbent resin particles was determined from the following equation:

water-retention capacity of physiological saline (g/g)
=[$Wa-Wb$](g)/mass of water-absorbent resin particles (g)

(2) Median Particle Size

About 50 g of water-absorbent resin particles was allowed to pass through a JIS standard sieve with opening of 250 μm. When 50% by mass or more of the particles were passed through the sieve, the combination of sieves (A) was used to measure the median particle size; when less than 50% by mass of the particles were passed through the sieve, the combination of sieves (B) was used to measure the median particle size.
(A) JIS standard sieves were combined in the following order: from the top, a sieve with opening of 500 μm, a sieve with opening of 250 μm, a sieve with opening of 180 μm, a sieve with opening of 150 μm, a sieve with opening of 106 μm, a sieve with opening of 75 μm, a sieve with opening of 45 μm, and a receiving tray.

(B) JIS standard sieves were combined in the following order: from the top, a sieve with opening of 850 μm, a sieve with opening of 600 μm, a sieve with opening of 500 μm, a sieve with opening of 425 μm, a sieve with opening of 300 μm, a sieve with opening of 250 μm, a sieve with opening of 150 μm, and a receiving tray.

About 50 g of the water-absorbent resin particles was placed in the top sieve of the combination sieves, and shaken with a rotating-tapping shaker for 10 minutes for classification. After classification, the mass of the water-absorbent resin particles remained in each sieve was calculated as mass percentage of the entire water-absorbent resin particles, and integrated in order from the large particle size. Subsequently, the correlation between the opening sizes of the sieves and the cumulative values calculated as mass percentage of the water-absorbent resin particles remaining in the sieves were dotted on logarithmic probability paper. The dots on the paper were connected to form a straight line, and the particle size at which the cumulative mass percentage is 50% by mass was determined to be the median particle size.

(3) Uniformity Degree of Particle Size Distribution

In the section (2) Median Particle Size, particle size (X1) corresponding to the cumulative mass percentage of 15.9% by mass and particle size (X2) corresponding to the cumulative mass percentage of 84.1% by mass were calculated, and the uniformity degree was determined from the following equation:

uniformity degree=$X1/X2$

The uniformity degree closer to 1.0 indicates a narrower particle size distribution.

Example 1

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 321 g (472 ml) of n-heptane was placed in this flask, and then 0.92 g of glyceryl monolaurate acetate with an HLB of 2.0 (Riken Vitamin Co., Ltd., Poem G-002) was added thereto as a dispersion stabilizer. The mixture was heated to 80° C. with stirring to dissolve the dispersion stabilizer, and then cooled to 65° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.27 g of hydroxyethyl cellulose (Sumitomo Seika Chemicals Co., Ltd., AW-15F) as a thickener, 0.11 g (0.41 mmoles) of potassium persulfate as a radical polymerization initiator, and 9.2 mg (0.05 mmoles) of ethylene glycol diglycidyl ether as an internal crosslinking agent were added thereto and dissolved, thereby preparing a monomer aqueous solution.

The monomer aqueous solution was added to the separable flask, and maintained at 45° C. for 30 minutes with the stirrer rotation set at 700 r/min, while the atmosphere of the system was being replaced with nitrogen. Subsequently, the flask was immersed in a water bath at 70° C. to increase the temperature, and polymerization was allowed to proceed for 60 minutes.

After polymerization, the rotation of the stirrer was changed to 1,000 r/min, the flask was immersed in an oil bath at 125° C. to increase the temperature, and 125.7 g of water was removed to the outside of the system under reflux of n-heptane by azeotropic distillation of water and n-heptane. Subsequently, 3.68 g of a 2% by mass aqueous solution of ethylene glycol diglycidyl ether was added thereto as a post-crosslinking agent, and water and n-heptane were continuously removed by distillation, followed by drying, thereby obtaining 97.1 g of spherical water-absorbent resin particles. The physical properties of the water-absorbent resin particles were evaluated in accordance with the procedures described above. Table 1 shows the results.

Example 2

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 321 g (472 ml) of n-heptane was placed in this flask, and then 0.92 g of glyceryl monostearate citrate with an HLB of 9.5 (Taiyo Kagaku Co., Ltd., Sunsoft No. 621B) as a dispersion stabilizer, and 0.92 g of a maleic anhydride modified ethylene-propylene copolymer (Mitsui Chemicals, Inc., Hi-WAX 1105A) as a polymeric dispersion stabilizer were added thereto. The mixture was heated to 80° C. with stirring to dissolve the dispersion stabilizer, and then cooled to 65° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.27 g of hydroxyethyl cellulose (Sumitomo Seika Chemicals Co., Ltd., AW-15F) as a thickener, 0.11 g (0.41 mmoles) of potassium persulfate as a radical polymerization initiator, and 9.2 mg (0.05 mmoles) of ethylene glycol diglycidyl ether as an internal crosslinking agent were added thereto and dissolved, thereby preparing a monomer aqueous solution.

The monomer aqueous solution was added to the separable flask, and maintained at 45° C. for 30 minutes with the stirrer rotation set at 700 r/min, while the atmosphere of the system was being replaced with nitrogen. Subsequently, the flask was immersed in a water bath at 70° C. to increase the temperature, and polymerization was allowed to proceed for 60 minutes.

After polymerization, the rotation of the stirrer was changed to 1,000 r/min, the flask was immersed in an oil bath at 125° C. to increase the temperature, and 125.7 g of water was removed to the outside of the system under reflux of n-heptane by azeotropic distillation of water and n-heptane. Subsequently, 3.68 g of a 2% by mass aqueous solution of ethylene glycol diglycidyl ether was added thereto as a post-crosslinking agent, and water and n-heptane were continuously removed by distillation, followed by drying, thereby obtaining 97.5 g of spherical water-absorbent resin particles. The physical properties of the water-absorbent resin particles were evaluated in accordance with the procedures described above. Table 1 shows the results.

Example 3

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 321 g (472 ml) of n-heptane was placed in this flask, and then 0.92 g of glyceryl monolaurate acetate with an HLB of 2.0 (Riken Vitamin Co., Ltd., Poem G-002) as a dispersion stabilizer, and 0.92 g of a maleic anhydride modified ethylene-propylene copolymer (Mitsui Chemicals, Inc., Hi-WAX 1105A) as a polymeric dispersion stabilizer were added thereto. The mixture was heated to 80° C. with stirring to dissolve the dispersion stabilizer, and then cooled to 65° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.27 g of hydroxyethyl cellulose (Sumitomo Seika Chemicals Co., Ltd., AW-15F) as a thickener, 0.11 g (0.41 mmoles) of potassium persulfate as a radical polymerization initiator, and 9.2 mg (0.05 mmoles) of ethylene glycol diglycidyl ether as an internal crosslinking agent were added thereto and dissolved, thereby preparing a monomer aqueous solution of the first step.

The monomer aqueous solution of the first step was added to the separable flask, and maintained at 45° C. for 30 minutes with the stirrer rotation set at 700 r/min, while the atmosphere of the system was being replaced with nitrogen. Subsequently, the flask was immersed in a water bath at 70° C. to increase the temperature, and polymerization of the first step was allowed to proceed for 60 minutes. After polymerization, a slurry was obtained.

128.2 g (1.43 moles) of an 80.5% by mass acrylic acid aqueous solution and 30.5 g of ion-exchanged water were placed in a 500-mL Erlenmeyer flask, and 143.3 g of a 30% by mass sodium hydroxide aqueous solution was added dropwise thereto with external cooling to thereby neutralize 75 mol % of the acid groups. Thereafter, 0.15 g (0.56 mmoles) of potassium persulfate as a radical polymerization initiator, and 12.8 mg (0.07 mmoles) of ethylene glycol diglycidyl ether as an internal crosslinking agent were added thereto and dissolved, thereby preparing a monomer aqueous solution of the second step.

After the rotation of the stirrer was changed to 1,000 r/min, the monomer aqueous solution of the second step was added to the separable flask, and maintained at 20° C. for 30 minutes while the atmosphere of the system was being replaced with nitrogen. Subsequently, the flask was immersed in a water bath at 70° C. to increase the temperature, and polymerization of the second step was allowed to proceed for 30 minutes.

After polymerization of the second step, the flask was immersed in an oil bath at 125° C. to increase the temperature, and 258.5 g of water was removed to the outside of the system under reflux of n-heptane by azeotropic distillation of water and n-heptane. Subsequently, 3.96 g of a 2% by mass aqueous solution of ethylene glycol diglycidyl ether was added thereto as a post-crosslinking agent, and water and n-heptane were continuously removed by distillation, followed by drying, thereby obtaining 241.9 g of water-absorbent resin particles in the form of agglomerated spherical particles. The physical properties of the water-absorbent resin particles were evaluated in accordance with the procedures described above. Table 1 shows the results.

Example 4

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 321 g (472 ml) of n-heptane was placed in this flask, and then 0.92 g of glyceryl monostearate lactate with an HLB of 7.5 (Taiyo Kagaku Co., Ltd., Sunsoft No. 661AS) as a dispersion stabilizer and 0.92 g of a maleic anhydride modified ethylene-propylene copolymer (Mitsui Chemicals, Inc., Hi-WAX 1105A) as a polymeric dispersion stabilizer were added thereto. The mixture was heated to 80° C. with stirring to dissolve the dispersion stabilizer, and then cooled to 65° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.27 g of hydroxyethyl cellulose (Sumitomo Seika Chemicals Co., Ltd., AW-15F) as a thickener, 0.11 g (0.41 mmoles) of potassium persulfate as a radical polymerization initiator, and 9.2 mg (0.05 mmoles) of ethylene glycol diglycidyl ether as an internal crosslinking agent were added thereto and dissolved, thereby preparing a monomer aqueous solution of the first step.

The monomer aqueous solution of the first step was added to the separable flask, and maintained at 45° C. for 30 minutes with the stirrer rotation set at 700 rpm, while the atmosphere of the system was being replaced with nitrogen. Subsequently, the flask was immersed in a water bath at 70° C. to increase the temperature, and polymerization of the first step was allowed to proceed for 60 minutes. After polymerization, a slurry was obtained.

128.2 g (1.43 moles) of an 80.5% by mass acrylic acid aqueous solution and 30.5 g of ion-exchanged water were placed in a 500-mL Erlenmeyer flask, and 143.3 g of a 30% by mass sodium hydroxide aqueous solution was added dropwise thereto with external cooling to thereby neutralize 75 mol % of the acid groups. Thereafter, 0.15 g (0.56 mmoles) of potassium persulfate as a radical polymerization initiator, and 12.8 mg (0.07 mmoles) of ethylene glycol diglycidyl ether as an internal crosslinking agent were added thereto and dissolved, thereby preparing a monomer aqueous solution of the second step.

After the rotation of the stirrer was changed to 1,000 r/min, the monomer aqueous solution of the second step was added to the separable flask, and maintained at 20° C. for 30 minutes while the atmosphere of the system was being replaced with nitrogen. Subsequently, the flask was immersed in a water bath at 70° C. to increase the temperature, and polymerization of the second step was allowed to proceed for 30 minutes.

After polymerization of the second step, the flask was immersed in an oil bath at 125° C. to increase the temperature, and 258.5 g of water was removed to the outside of the system under reflux of n-heptane by azeotropic distillation of water and n-heptane. Subsequently, 3.96 g of a 2% by mass aqueous solution of ethylene glycol diglycidyl ether was added thereto as a post-crosslinking agent, and water and n-heptane were continuously removed by distillation, followed by drying, thereby obtaining 242.1 g of water-absorbent resin particles in the form of agglomerated spherical particles. The physical properties of the water-absorbent resin particles were evaluated in accordance with the procedures described above. Table 1 shows the results.

Comparative Example 1

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 321 g (472 ml) of n-heptane was placed in this flask, and then 0.92 g of tetra glycerin stearic acid ester with an HLB of 4 (Mitsubishi-Kagaku Foods Corporation, Ryoto Polygly TS-4) as a dispersion stabilizer and 0.92 g of a maleic anhydride modified ethylene-propylene copolymer (Mitsui Chemicals, Inc., Hi-WAX 1105A) as a polymeric dispersion stabilizer were added thereto. The mixture was heated to 80° C. with stirring to dissolve the dispersion stabilizer, and then cooled to 55° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.27 g of hydroxyethyl cellulose (Sumitomo Seika Chemicals Co., Ltd., AW-15F) as a thickener, 0.11 g (0.41 mmoles) of potassium persulfate as a radical polymerization initiator, and 9.2 mg (0.05 mmoles) of ethylene glycol diglycidyl ether as an internal crosslinking agent were added thereto and dissolved, thereby preparing a monomer aqueous solution.

The monomer aqueous solution was added to the separable flask, and maintained at 35° C. for 30 minutes with the stirrer rotation set at 700 r/min, while the atmosphere of the system was being replaced with nitrogen. Subsequently, the flask was immersed in a water bath at 70° C. to increase the temperature, and polymerization was allowed to proceed for 60 minutes.

After polymerization, the rotation of the stirrer was changed to 1,000 r/min. The flask was immersed in an oil bath at 125° C. to increase the temperature, and 125.7 g of water was removed to the outside of the system under reflux of n-heptane by azeotropic distillation of water and n-heptane. Subsequently, 3.68 g of a 2% by mass aqueous solution of ethylene glycol diglycidyl ether was added thereto as a post-crosslinking agent, and water and n-heptane were continuously removed by distillation, followed by drying, thereby obtaining 97.0 g of spherical water-absorbent resin particles. The physical properties of the water-absorbent resin particles were evaluated in accordance with the procedures described above. Table 1 shows the results.

Comparative Example 2

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 321 g (472 ml) of n-heptane was placed in this flask, and then 0.92 g of tetra glycerin stearic acid ester with an HLB of 4 (Mitsubishi-Kagaku Foods Corporation, Ryoto Polygly TS-4) as a dispersion stabilizer and 0.92 g of a maleic anhydride modified ethylene-propylene copolymer (Mitsui Chemicals, Inc., Hi-WAX 1105A) as a polymeric dispersion stabilizer were added thereto. The mixture was heated to 80° C. with stirring to dissolve the dispersion stabilizer, and then cooled to 55° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.27 g of hydroxyethyl cellulose (Sumitomo Seika Chemicals Co., Ltd., AW-15F) as a thickener, 0.11 g (0.41 mmoles) of potassium persulfate as a radical polymerization initiator, and 9.2 mg (0.05 mmoles) of ethylene glycol diglycidyl ether as an internal crosslinking agent were added thereto and dissolved, thereby preparing a monomer aqueous solution of the first step.

The monomer aqueous solution of the first step was added to the separable flask, and maintained at 35° C. for 30 minutes with the stirrer rotation set at 450 r/min, while the atmosphere of the system was being replaced with nitrogen. Subsequently, the flask was immersed in a water bath at 70° C. to increase the temperature, and polymerization of the first step was allowed to proceed for 60 minutes. After polymerization, a slurry was obtained.

128.2 g (1.43 moles) of an 80.5% by mass acrylic acid aqueous solution and 30.5 g of ion-exchanged water were placed in a 500-mL Erlenmeyer flask, and 143.3 g of a 30% by mass sodium hydroxide aqueous solution was added dropwise thereto with external cooling to thereby neutralize 75 mol % of the acid groups. Thereafter, 0.15 g (0.56 mmoles) of potassium persulfate as a radical polymerization initiator and 12.8 mg (0.07 mmoles) of ethylene glycol diglycidyl ether as an internal crosslinking agent were added thereto and dissolved, thereby preparing a monomer aqueous solution of the second step.

After the rotation of the stirrer was changed to 1,000 r/min, the monomer aqueous solution of the second step was added to the separable flask, and maintained at 25° C. for 30 minutes while the atmosphere of the system was being replaced with nitrogen. Subsequently, the flask was immersed in a water bath at 70° C. to increase the temperature, and polymerization of the second step was allowed to proceed for 30 minutes.

After polymerization of the second step, the flask was immersed in an oil bath at 125° C. to increase the temperature, and 267.8 g of water was removed to the outside of the system under reflux of n-heptane by azeotropic distillation of water and n-heptane. Subsequently, 3.96 g of a 2% by mass aqueous solution of ethylene glycol diglycidyl ether was added thereto as a post-crosslinking agent, and water and n-heptane were continuously removed by distillation, followed by drying, thereby obtaining 242.5 g of water-absorbent resin particles in the form of agglomerated spherical particles. The physical properties of the water-absorbent resin particles were evaluated in accordance with the procedures described above. Table 1 shows the results.

Comparative Example 3

A 2-L round-bottom cylindrical separable flask with an inner diameter of 100 mm, equipped with a reflux condenser, a dropping funnel, a nitrogen gas inlet tube, a stirrer, and stirring blades (two sets of four inclined paddle blades with a blade diameter of 50 mm) was used in this Example. 378 g (472 ml) of cyclohexane was placed in this flask, and then 0.92 g of sorbitan monostearate with an HLB of 4.7 (Kao Corporation, Rheodol SP-10V) as a dispersion stabilizer and 0.92 g of a maleic anhydride modified ethylene-propylene copolymer (Mitsui Chemicals, Inc., Hi-WAX 1105A) as a polymeric dispersion stabilizer were added thereto. The mixture was heated to 80° C. with stirring to dissolve the dispersion stabilizer, and then cooled to 55° C.

92 g (1.03 moles) of an 80.5% by mass acrylic acid aqueous solution and 51.2 g of ion-exchanged water were placed in a 500-mL Erlenmeyer flask, and 102.9 g of a 30% by mass sodium hydroxide aqueous solution was added dropwise thereto with external cooling to thereby neutralize 75 mol % of the acid groups. Thereafter, 0.11 g (0.41 mmoles) of potassium persulfate as a radical polymerization initiator, and 2.3 mg (0.01 mmoles) of N,N'-methylene bisacrylamide as an internal crosslinking agent were added thereto and dissolved, thereby preparing a monomer aqueous solution.

The monomer aqueous solution was added to the separable flask, and maintained at 35° C. for 30 minutes with the stirrer rotation set at 250 r/min, while the atmosphere of the system was being replaced with nitrogen. Subsequently, the flask was immersed in a water bath at 70° C. to increase the temperature, and polymerization was allowed to proceed for 60 minutes.

After polymerization, the rotation of the stirrer was changed to 1,000 r/min. The flask was immersed in an oil bath at 125° C. to increase the temperature, and 125.7 g of water was removed to the outside of the system under reflux of cyclohexane by azeotropic distillation of water and cyclohexane. Subsequently, 3.68 g of a 2% by mass aqueous solution of ethylene glycol diglycidyl ether was added thereto as a post-crosslinking agent, and water and cyclohexane were continuously removed by distillation, followed by drying, thereby obtaining 70.3 g of water-absorbent resin particles in the form of partially agglomerated spherical particles. The physical properties of the water-absorbent resin particles were evaluated in accordance with the procedures described above. Table 1 shows the results.

TABLE 1

| | Dispersion stabilizer | Median Particle Size (μm) | Uniformity degree of Particle Size Distribution | Water-retention capacity of physiological saline (g/g) |
|---|---|---|---|---|
| Example 1 | Glyceryl Monolaurate Acetate | 84 | 2.2 | 39 |
| Example 2 | Glyceryl Monostearate Citrate | 66 | 2.0 | 36 |
| Example 3 | Glyceryl Monolaurate Acetate | 380 | 1.7 | 36 |
| Example 4 | Glyceryl Monostearate Lactate | 360 | 1.9 | 35 |
| Comparative Example 1 | Tetra Glycerin Stearic Acid Ester | 57 | 3.3 | 35 |
| Comparative Example 2 | Tetra Glycerin Stearic Acid Ester | 390 | 3.8 | 37 |
| Comparative Example 3 | Sorbitan Monostearate | 220 | 3.5 | 33 |

The results shown in Table 1 reveal that the water-absorbent resin particles obtained in each of the Examples have suitable water-retention capacity (water absorption capacity), suitable particle size, and narrow particle size distribution.

INDUSTRIAL APPLICABILITY

The method according to the present invention can provide water-absorbent resin particles that exhibit an excellent water-absorption ability with a suitable particle size and narrow particle size distribution, and that can suitably be used in absorbent articles, such as sanitary napkins, incontinence pads, and disposable diapers.

The invention claimed is:

1. A method for producing water-absorbent resin particles by subjecting a water-soluble ethylenically unsaturated monomer to reversed-phase suspension polymerization in a dispersion medium, the method comprising performing the reversed-phase suspension polymerization in the presence of an organic acid monoglyceride,
wherein the organic acid monoglyceride is a compound in which a fatty acid is ester-bonded with one of three hydroxyl groups in glycerol, and at least one of the glycerol's two remaining hydroxyl groups is ester bonded with an organic acid.

2. The method for producing water-absorbent resin particles according to claim 1, wherein the organic acid monoglyceride has one ester group in which a fatty acid having 10 to 18 carbon atoms is ester-bonded with one hydroxyl group of the glycerol, and one or two ester groups in which an organic acid having 2 to 8 carbon atoms is ester-bonded with one or two hydroxyl groups of the glycerol.

3. The method for producing water-absorbent resin particles according to claim 2, wherein the fatty acid having 10 to 18 carbon atoms is at least one member selected from the group consisting of capric acid, lauric acid, myristic acid, palmitic acid, stearic acid, and oleic acid.

4. The method for producing water-absorbent resin particles according to claim 2, wherein the organic acid having 2 to 8 carbon atoms is at least one member selected from the group consisting of acetic acid, lactic acid, citric acid, succinic acid, and diacetyl tartaric acid.

5. The method for producing water-absorbent resin particles according to claim 1, wherein the organic acid monoglyceride is at least one member selected from the group consisting of glyceryl monolaurate acetate, glyceryl monostearate acetate, glyceryl monostearate lactate, glyceryl monostearate citrate, and glyceryl monooleate citrate.

6. The method for producing water-absorbent resin particles according to claim 1, wherein the amount of the organic acid monoglyceride is 0.1 to 30 parts by mass per 100 parts by mass of the water-soluble ethylenically unsaturated monomer.

7. The method for producing water-absorbent resin particles according to claim 1, wherein the reversed-phase suspension polymerization is performed in the presence of a radical polymerization initiator.

8. The method for producing water-absorbent resin particles according to claim 1, wherein the dispersion medium is a hydrocarbon dispersion medium.

9. The method for producing water-absorbent resin particles according to claim 1, the method comprising, after the reversed-phase suspension polymerization, adding a crosslinking agent to perform post-crosslinking.

10. The method for producing water-absorbent resin particles according to claim 1, wherein the water-soluble ethylenically unsaturated monomer is at least one member selected from the group consisting of (meth)acrylic acid, salts thereof, (meth)acrylamide, and N,N-dimethyl(meth) acrylamide.

11. The method for producing water-absorbent resin particles according to claim 3, wherein the organic acid having 2 to 8 carbon atoms is at least one member selected from the group consisting of acetic acid, lactic acid, citric acid, succinic acid, and diacetyl tartaric acid.

12. The method for producing water-absorbent resin particles according to claim 11, wherein the amount of the organic acid monoglyceride is 0.1 to 30 parts by mass per 100 parts by mass of the water-soluble ethylenically unsaturated monomer.

13. The method for producing water-absorbent resin particles according to claim 12, wherein the water-soluble ethylenically unsaturated monomer is at least one member selected from the group consisting of (meth)acrylic acid, salts thereof, (meth)acrylamide, and N,N-dimethyl(meth)acrylamide.

14. The method for producing water-absorbent resin particles according to claim 5, wherein the amount of the organic acid monoglyceride is 0.1 to 30 parts by mass per 100 parts by mass of the water-soluble ethylenically unsaturated monomer.

15. The method for producing water-absorbent resin particles according to claim 14, wherein the water-soluble ethylenically unsaturated monomer is at least one member selected from the group consisting of (meth)acrylic acid, salts thereof, (meth)acrylamide, and N,N-dimethyl(meth)acrylamide.

16. The method for producing water-absorbent resin particles according to claim 15, wherein the inverse suspension polymerization is performed in the presence of a radical polymerization initiator.

17. The method for producing water-absorbent resin particles according to claim 16, wherein the dispersion medium is a hydrocarbon dispersion medium.

18. The method for producing water-absorbent resin particles according to claim 17, the method comprising, after the inverse suspension polymerization, adding a crosslinking agent to perform post-crosslinking.

\* \* \* \* \*